United States Patent [19]
van't Riet et al.

[11] Patent Number: 5,183,828
[45] Date of Patent: Feb. 2, 1993

[54] POLYHYDROXYBENZOIC ACID DERIVATIVES

[76] Inventors: Bartholomeus van't Riet, 3419 Noble Ave., Richmond, Va. 23222; Howard L. Elford, 3313 Gloucester Rd., Richmond, Va. 23227; Galen L. Wampler, 6938 Chamberlayne Rd., Mechanicsville, Va. 23111

[21] Appl. No.: 555,834

[22] Filed: Jul. 20, 1990

Related U.S. Application Data

[60] Continuation-in-part of Ser. No. 302,946, Jan. 30, 1989, abandoned, which is a division of Ser. No. 907,562, Sep. 15, 1986, Pat. No. 4,942,253, which is a division of Ser. No. 497,370, May 23, 1983, Pat. No. 4,623,659.

[51] Int. Cl.$^5$ ............... A61K 31/215; A61K 31/275; A61K 31/155; A61K 31/165
[52] U.S. Cl. ................... 514/508; 514/519; 514/617; 514/633; 514/637; 558/423; 558/6; 564/177; 564/229; 564/247
[58] Field of Search .............. 514/508, 519, 633

[56] References Cited

U.S. PATENT DOCUMENTS 4,623,659 11/1986 van't Riet .................... 514/508

OTHER PUBLICATIONS

Morrison & Boyd, Organic Chemistry, (2nd Ed.), Allyn & Bacon, Boston, pp. 42–43, 1181.
Broner et al., Critical Care Medicine, 16, 848, (1988), Ad, CR Val-Pak, Indianapolis.
Ding et al., Ann. Thoracic Surg., 53, 1091 (1992).

Primary Examiner—Frederick E. Waddell
Assistant Examiner—T. J. Criares
Attorney, Agent, or Firm—James L. Rowe

[57] ABSTRACT

Polyhydroxy-substituted benz, phenylacet and mandelamidines, amidates, amidoximes and hydroxyamidoximes—ribonucleotide reductase inhibitors, and free radical scavengers.

2 Claims, No Drawings

POLYHYDROXYBENZOIC ACID DERIVATIVES

CROSS-REFERENCE

This application is a continuation-in-part of our copending application Ser. No. 302,946, filed Jan. 30, 1989, now abandoned, which was in turn a division of our then copending application Ser. No. 907,562, filed Sep. 15, 1986, now U.S. Pat. No. 4,942,253, issued Jul. 17, 1990, which application was in turn a division of our then copending application Ser. No. 497,370, filed May 23, 1983, now U.S. Pat. No. 4,623,659, issued Nov. 18, 1986.

BACKGROUND OF THE INVENTION

Various hydroxy substituted benzohydroxamic acids are known—see Gale and Hynes, *J. Med. Chem.*, 11, 191 (1968), Gale, Hynes and Smith, ibid, 13, 571 (1970), van't Riet, et al., U.S. Pat. No. 4,263,322, Howle and Gale, *Proc. Soc. Exptl. Biol. Med.*, 131, 697 (1969), Gale, et al., *Biochem. Pharm.*, 20, 2677 (1971).

Biological effects of hydroxy-substituted benzamides as well as other uses of such compounds are found in Kreuchunas, U.S. Pat. No. 2,849,480, *Chemical Abstracts*, 85, 94115w (1978), 74, 112752f (1971).

The hydroxybenzohydroxamic acids are known to be inhibitors of ribonucleotide reductase according to the Elford, Wampler and van't Riet group—see *Cancer Res.*, 22, 589 (1979), Abstracts, *Proc. Am. Assoc. Cancer Res.*, 18, 177 (1977), 19, 63 (1978), 20, 149 (1979), 22, 18 (1981), 23, 202 (1982), Va. J. Sci., 29, 81 (1978), papers, *J. Pharm. Sci.*, 69, 856 (1980), New Approaches to the Design of Antineoplastic Agents-Bardos and Kalman, eds., pp. 227 (Elsevier Biomedical, New York, N.Y.), 856 (1982), *Advances in Enzyme Regulation*, 19, 151 (1981), Abstract, *Med. Ped. Oncol.*, 10, 102 (1982), Abstract, *Proc. 13th Int. Cancer Cong.*, pp. 88 (1982), papers, *J. Med. Chem.*, 22, 589 (1979) and *Cancer Treat. Rep.*, 66, 1825 (1982).

Polyhydroxy-substituted benzamidoximes, benzamidines, benzohydroxyamidoximes and benzamidates, so far as can be ascertained, are not recorded in the chemical literature.

SUMMARY OF THE INVENTION

This invention provides compounds of the formula:

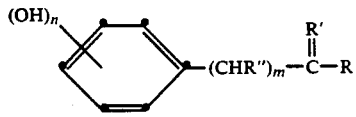

wherein n is 2–5, m is 0 or 1, R' is NOH or NH, R is $NH_2$ or NHOH when R' is NOH, R is $NH_2$ or $O\text{-}C_{1\text{-}3}$ alkyl when R' is NH, and R" is H or OH; and pharmaceutically acceptable acid addition salts thereof.

Preferred compounds according to formula I are those in which at least two of the hydroxyls in the phenyl ring are vicinal. An even more preferred group of compounds are those in which the vicinal hydroxyls are at C-3 and C-4 of the phenyl ring.

Compounds according to I are named as hydroxy-substituted benzamidoximes when m is O, R' is NOH and R is $NH_2$, as hydroxy-substituted benzohydroxyamidoximes when m is O, R' is NOH and R is NHOH, as hydroxy-substituted benzamidates when m is O, R' is NH and R is $O\text{-}C_{1\text{-}3}$ alkyl and as hydroxy-substituted benzamidines when m is O, R' is NH and R is $NH_2$.

When m is 1, and R" is OH, the compounds are named as hydroxy-substituted mandelamidoximes, mandelohydroxyamidoximes, mandelamidates and mandelamidines respectively. These mandelic acid derivatives have a center of assymetry and hence are prepared as a racemate or dl mixture. This invention includes both the racemates as well as the individual component optical isomers.

When m is 1 and R" is H, the compounds are named as hydroxy-substituted phenylacetamidoximes, phenylacetohydroxyamidoximes, phenylacetamidates and phenylacetamidines respectively.

Representative compounds according to formula I above include:

2,3-dihydroxybenzohydroxyamidoxime
3,4-dihydroxybenzohydroxyamidoxime
methyl 2,3,4-trihydroxybenzamidate
isopropyl 3,5-dihydroxybenzamidate
ethyl 3,4,5-trihydroxybenzamidate
ethyl 3,4-dihydroxybenzamidate
3,4-dihydroxybenzamidoxime
3,4,5-trihydroxybenzamidoxime
2,3,5-trihydroxybenzamidoxime
n-propyl 2,4,5-trihydroxybenzamidate
2,3-dihydroxybenzamidoxime
ethyl 2,4-dihydroxybenzamidate
ethyl 3,4,5-trihydroxybenzamidate
2,5-dihydroxybenzohydroxyamidoxime
3,4,5-trihydroxybenzamidine
2,3-dihydroxybenzamidine
2,3,4-trihydroxybenzamidine
3,4-dihydroxybenzamidine
dl-2,4,5-trihydroxymandelamidine
2,4,5-trihydroxybenzamidine
3,5-dihydroxybenzamidine
dl-3,4-dihydroxymandelamidine
dl-3,4,5-trihydroxymandelamidine
dl-2,3-dihydroxymandelamidine
dl-2,3,4-trihydroxymandelohydroxyamidoxime
dl-2,4,5-trihydroxymandelohydroxyamidoxine
2,3,4-trihydroxybenzamidoxime
2,3,4-trihydroxybenzohydroxyamidoxime
3,4,5-trihydroxybenzohydroxyamidoxime
ethyl 2,3-dihydroxybenzamidate
dl-3,4-dihydroxymandelamidoxime
dl-3,4,5-trihydroxymandelohydroxyamidoxime
dl-3,5-dihydroxymandelohydroxyamidoxime
dl-3,4-dihydroxymandelohydroxyamidoxime
dl-2,4-dihydroxymandelamidoxime
dl-2,3-dihydroxymandelamidoxime
dl-3,5-dihydroxymandelamidoxime
dl-2,3,4-trihydroxymandelamidoxime
dl-3,4,5-trihydroxymandelamidoxime
dl-2,4,5-trihydroxymandelamidoxime
dl-methyl 3,4-dihydroxymandelamidate
dl-ethyl 3,5-dihydroxymandelamidate
dl-n-propyl 2,3-dihydroxymandelamidate
dl-methyl 2,3,4-trihydroxymandelamidate
dl-ethyl 3,4,5-trihydroxymandelamidate
dl-ethyl 2,3,5-trihydroxymandelamidate
dl-isopropyl 2,4,5-trihydroxymandelamidate
3,4-dihydroxyphenylacetamidoxime
3,5-dihydroxyphenylacetamidoxime
2,3-dihydroxyphenylacetamidoxime
2,5-dihydroxyphenylacetamidoxime
2,4-dihydroxyphenylacetamidoxime 2,3,4-trihydroxyphenylacetamidoxime
3,4,5-trihydroxyphenylacetamidoxime
2,4,5-trihydroxyphenylacetamidoxime
2,3,5-trihydroxyphenylacetamidoxime
ethyl 3,4-dihydroxyphenylacetamidate
methyl 2,3-dihydroxyphenylacetamidate
n-propyl 3,5-dihydroxyphenylacetamidate
isopropyl 2,3,4-trihydroxyphenylacetamidate
methyl 3,4,5-trihydroxyphenylacetamidate
methyl 2,4,5-trihydroxyphenylacetamidate
methyl 2,3,4,5-tetrahydroxyphenylacetamidate
ethyl 2,3,4,6-tetrahydroxyphenylacetamidate
methyl 2,3,4,5,6-pentahydroxyphenylacetamidate
2,3,4,5-tetrahydroxyphenylacetamidine
2,3,4,6-tetrahydroxybenzylacetamidine
2,3,5,6-tetrahydroxyphenylacetamidine
2,3,4,5,6-pentahydroxyphenylacetamidine
2,3,4,5,6-pentahydroxyphenylacetohydroxyamidoxime
2,3,5,6-tetrahydroxyphenylacetohydroxyamidoxime
2,3,4,5-tetrahydroxyphenylacetohydroxyamidoxime
ethyl 2,3,5-trihydroxyphenylacetamidate
2,3-dihydroxyphenylacetamidine
3,4-dihydroxyphenylacetamidine
3,5-dihydroxyphenylacetamidine
2,4-dihydroxyphenylacetamidine
2,5-dihydroxyphenylacetamidine
2,3,4-trihydroxyphenylacetamidine
3,4,5-trihydroxyphenylacetamidine
2,4,5-trihydroxyphenylacetamidine
2,3,5-trihydroxyphenylacetamidine
3,4-dihydroxyphenylacetohydroxyamidoxime
3,5-dihydroxyphenylacetohydroxyamidoxime
2,3-dihydroxyphenylacetohydroxyamidoxime
2,3,4-trihydroxyphenylacetohydroxyamidoxime
2,3,5-trihydroxyphenylacetohydroxyamidoxime
2,4,5-trihydroxyphenylacet.hoydroxyamidoxime
3,4,5-trihydroxyphenylacetohydroxyamidoxime, and
the like.

Benzamidoximes and phenylacetamidoximes according to I above, where R' is NOH and R is NH₂, can be prepared reacting a nitrile of the formula

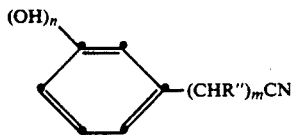

where m is 0 or 1 and R" is H with hydroxylamine in aqueous solution. Where R" is OH and m is 1, this nitrile may be a transitory intermediate formed by reacting an aldehyde of the formula

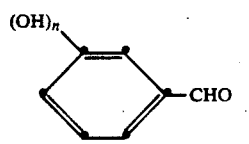

where n is 2-5 with a mixture of an alkali metal cyanide and hydroxylamine hydrochloride in aqueous solution. The mandelonitrile (a cyanohydrin) forms initially but then reacts at once with hydroxylamine to give the desired mandelamidoxime.

The amidates (I where R is O-C₁₋₃ alkyl and R' is NH) can be prepared by reacting the above nitrile (II) with a lower alkanol (C₁₋₃ alkylOH) to which has been added an acid such as gaseous HCl. The reaction medium here should be non-aqueous, and Lewis acids other than HCl can be employed.

Nitriles useful in the above two synthetic procedures are readily available by processes set forth in the art. 2,3,4-Trihydroxybenzonitrile, the three tetrahydroxybenzonitriles and pentahydroxybenzonitrile are, however, new and their synthesis will be set forth in detail below.

Compounds according to I in which R is NHOH and R' is NOH can be prepared from the corresponding benzamidoxime, phenylacetamidoxime or mandelamidoxime

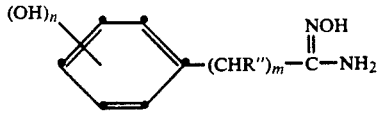

when n, m and R" have the same significance as before by reaction with hydroxylamine hydrochloride. The hydroxy-substituted benzamidines, phenylacetamidines and mandelamidines can be prepared from the corresponding amidate by reaction with ethanolic ammonia.

The following more detailed examples illustrate the preparation of the compounds of this invention. Other equally useful methods for their preparation will readily suggest themselves to those skilled in the art.

EXAMPLE 1

Preparation of 3,4-Dihydroxybenzamidoxime 30 g. of 3,4-Dihydroxybenzonitrile were dissolved in 300 ml. of water containing 25 g. of hydroxylaminesulfate which had been neutralized by the addition of aqueous sodium hydroxide to pH = 8.0. The reaction mixture was stirred at about 45° C. for 18 hours. 3,4-Dihydroxybenzamidoxime formed in the above reaction had precipitated and was collected by filtration. The filtered amidoxime was suspended in water and the aqueous suspension acidified to about pH = 2.0 with 12N aqueous hydrochloric acid. The acidic solution was decolorized with charcoal and the solvent removed by evaporation. Recrystallization of the residue yielded 3,4-dihydroxybenzamidoximehydrochloride melting at about 193° C. with decomposition.

Analysis Calculated: C, 41.09; H, 4.43; N, 13.69;
Found: C, 41.12; H, 4.47; N, 13.69.
Equivalent weight by titration 206 (theory = 204.6); yield = 72%

EXAMPLE 2

Preparation of 3,4,5-Trihydroxybenzamidoxime

About 7.5 g. of 3,4,5-trihydroxybenzonitrile were dissolved in 200 ml. of water containing 7 g. of hydroxylamine sulfate which solution had previously been neutralized to about pH = 8.0 with aqueous sodium hydroxide. 2 g. of sodium sulfite were also present in solution. The reaction mixture was stirred at 45° C. for about 18 hours after which time the precipitated 3,4,5-trihydroxybenzamidoxime formed in the above reaction was collected. The product was converted to the hydrochloride salt and the hydrochloride salt purified by the process of Example 1. 3,4,5-Trihydroxybenzamidoxime hydrochloride thus prepared melted with decomposition at a temperature of about 206° C. after recrystallization from an isopropanol-ethyl acetate solvent mixture.
Analysis Calculated: C, 38.11; H, 4.11; N, 12.72;
Found: C, 38.16; H, 4.16; N, 12.66.
Equivalent weight by titration with aqueous sodium hydroxide=220 (theory=220.6; yield=80%

EXAMPLE 3

Preparation of Ethyl 3,4,5-Trihydroxybenzamidate 5 g. of 3,4,5-Trihydroxybenzonitrile were dissolved in ether. 2.2 ml. of ethanol were added. Next, anhydrous gaseous hydrogen chloride was passed through the solution. Ethyl 3,4,5-trihydroxybenzamidate hydrochloride formed in the above reaction precipitated. The precipitate was recrystallized from an isopropanolether solvent mixture. Ethyl 3,4,5-trihydroxybenzamidate hydrochloride thus prepared and purified melted at about 172° C. with decomposition.
Analysis Calculated: C, 46.26; H, 5.18; N, 5.99;
Found: C, 46.26; H, 5.22; N, 6.00.
Equivalent weight by titration with sodium hydroxide=115.5 (theory=116.8); yield=78%
Ethyl 3,4,5-trihydroxybenzamidate can be prepared by neutralization of the hydrochloride salt, extraction of the ester into ether and removal of the ether by evaporation.

EXAMPLE 4

Preparation of Ethyl 3,4-Dihydroxybenzamidate

Following the procedure of Example 3, 3,4-dihydroxybenzonitrile was converted to ethyl 3,4-dihydroxybenzamidate hydrochloride by the reaction with ethanol in the presence of hydrogen chloride. The compound melted at 170° C. with decomposition after recrystallization from an isopropanol/ether solvent mixture; yield=65%
Analysis Calculated: 49.67; H, 5.56; N, 6.44;
Found C, 49.91; H, 5.61; N, 6.45.

EXAMPLE 5

Preparation of Gallamidine

About 4.5 g. of ethyl 3,4,5-trihydroxybenzamidate hydrochloride were heated with an excess of 14N aqueous ammonium hydroxide in ethanol solution. The volatile constitutents were removed by evaporation and the residue, comprising gallamidine formed in the above reaction, was dissolved in alcohol. Gallamidine free base was converted to the hydrochloride salt by passing gaseous hydrogen chloride into the alcoholic solution. Gallamidine hydrochloride melted at about 169° C. with decomposition after recrystallization from an ethanol/ethyl acetate solvent mixture; yield=53%
Equivalent weight=203 by titration with aqueous sodium hydroxide (theory 204.5)
Analysis Calculated: C, 41.09; H, 4.43; N, 13.69;
Found: C, 40.80; H, 4.47; N, 14.30.

EXAMPLE 6

Preparation of 3,4-Dihydroxybenzohydroxyamidoxime

A solution of 5.5 g. of 3,4-dihydroxybenzamidoxime (from Example 1) was prepared in a minimal quantity of methanol. 3.5 g. of hydroxylamine hydrochloride were added. The reaction mixture was allowed to stand for about one day at about 50° C. Volatile constitutents were removed by evaporation. Ethyl acetate was added to the residue. The resulting precipitate was separated by filtration and gaseous hydrogen chloride passed into the filtrate. 3,4-Dihydroxybenzohydroxyamidoxime hydrochloride thus prepared was separated by filtration. The compound melted at about 169° C. with decomposition.
Equivalent weight by titration with sodium hydroxide=219 (theory=220.5)
Analysis Calculated: C, 38.11; H, 4.11; N, 12.70;
Found: C, 38.28; H, 4.15; N, 12.61.

EXAMPLE 7

Preparation of 3,4-Dihydroxymandelamidoxime

Seven and eight-tenths grams of 3,4-dihydroxybenzaldehyde were added to 100 ml. of an aqueous solution held at −15° C. containing 7.8 g. of hydroxylamine hydrochloride and 5.5 g. of sodium cyanide. The reaction mixture was stirred overnight at about 0° C. and then filtered. Four g. of 3,4-dihydroxymandelamidoxime monohydrate formed in the above reaction were obtained melting at 151° C. with decomposition (after loss of water of crystallization at about 120° C.) yield=36%
Analysis Calculated: C, 44.44; H, 5.60; H, 12.96;
Found: C, 44.37; H, 5.65; N, 12.92.

EXAMPLE 8

Preparation of 2,3,4-Trihydroxybenzamidoxime

Following the procedure of Example 2, 3.5 g. of 2,3,4-trihydroxybenzonitrile were reacted in 60 ml. of water with 4 g. of hydroxylamine sulfate and 2 g. of sodium bisulfite at pH=8.0 (adjusted by addition of concentrated aqueous sodium hydroxide). The reaction mixture was maintained at ambient temperature for about one hour and was then cooled. 2,3,4-Trihydroxybenzamidoxime precipitated and the precipitate was collected by filtration. The filter cake was dissolved in dilute aqueous hydrochloric acid and the resulting solution filtered through activated charcoal. Evaporation of the volatile constituents from the filtrate under reduced pressure yielded 2,3,4-trihydroxybenzamidoxime as a hydrochloride salt, melting at 207° C. with decomposition after recrystallization from a methanol/ethyl acetate solvent mixture; yield=9%.
Analysis Calculated: C, 38.11; H, 4.11; N, 12.72;
Found: C, 37.34; H, 4.06; N, 12.43.

The preparation of nitrile starting materials useful for preparing most of the compounds of this invention where the amide starting material is available or known is illustrated in the following example.

PREPARATION I

Preparation of Nitrile Starting Materials

A reaction mixture containing 23.5 g. of gallamide, 180 ml. of ethyl acetate and 35 ml. of thionylchloride was refluxed for about 18 hours. The volatile contents were removed by evaporation in vacuo and the resulting residue dissolved in 215 ml. of water. This aqueous solution was heated to about 90° C. until the evolution of gas had ceased. The aqueous solution was filtered through charcoal and the water removed from the filtrate by evaporation. 18 g. of Gallonitrile were obtained melting at about 219° C. with decomposition (86% yield). Other nitriles useful as starting materials can be prepared similarly.

PREPARATION II

Preparation of 2,3,4-Trihydroxybenzonitrile

Eighteen and five tenths grams of 2,3,4-trihydroxybenzamide were refluxed with 20 ml. of phosphorusoxychloride and 100 ml. of ethyl acetate for 2.5 hours. The volatile constituents were removed in vacuo and the residue poured into 150 ml. of an ice-water mixture. The resulting suspension was heated to 95° C. and then filtered through activated carbon. The filtrate was concentrated to about 50 ml. whereupon 2,3,4-trihydroxybenzonitrile precipitated and was collected by filtration. 2,3,4-Trihydroxybenzonitrile monohydrate thus prepared melted at 172° C. after recrystallization from a methanol-benzene solvent mixture; yield=57%

Analysis Calculated: C, 49.71; H, 4.17; N, 8.28;
Found: C, 49.70; H, 4.17; N, 8.27.

PREPARATION III

Preparation of 2,3,4,5-Tetrahydroxybenzonitrile

Following the procedure of Mayer et al., *Chem. Ber.*, 89, 511 (1956), 3,4,5-trimethoxybenzoic acid was brominated in ethyl acetate solution without added water using only 40% of the chloroform volume specified in that reference. Twenty-three and five tenths grams of 2-bromo-3,4,5-trimethoxybenzoic acid thus synthesized were added to a solution prepared by dissolving 1 g. of cupric acetate and 5 g. of sodium sulfite in 110 ml. of water followed by 27 g. of sodium hydroxide. The reaction mixture, which was a suspension, was heated to boiling for about six hours. Since it showed a tendency to solidify, extra water was added to maintain fluidity. At the end of six hours, the suspension was poured into a mixture of ice and 120 ml. of 12N aqueous hydrochloric acid. The volume was raised to about 900 ml. with water. This mixture was then heated. Complete dissolution occurred at about 95° C. at which point, 700 mg. of thioacetamide were added and heating continued until black copper sulfide had formed. The mixture was filtered through carbon. 3,4,5-Trimethoxysalicylic acid monohydrate precipitated from the filtrate.

The corresponding methyl ester was prepared by heating 3,4,5-trimethoxysalicylic acid monohydrate in methanol containing 2% sulfuric acid, as set forth in the above reference.

Methyl 3,4,5-trimethoxysalicylate prepared as above was heated in 14N aqueous ammonium hydroxide for four hours. The volatile constituents were removed in vacuo and the resulting residue, 3,4,5-trimethoxysalicylamide, was recrystallized from water at pH=5.0. The compound melted at about 151° C.; yield=70% (13.4 g. of 3,4,5-trimethoxy salicylic acid gave 9.3 g. of pure 3,4,5-trimethoxysalicylamide.) Seven and seven tenths grams of 3,4,5-trimethoxysalicylamide were heated to reflux with 8 ml. of phosphorusoxychloride in 100 ml. of ethyl acetate for about one hour. The volatile constituents were removed by evaporation in vacuo and the residue, comprising 3,4,5-trimethoxysalicylnitrile, was dissolved in water to which some ethanol was added until the solution was clear at 95° C. Again the volatile constituents were removed in vacuo and the liquid residue dissolved in hot benzene. The residue was dried and the solution used in the next demethylation step without further purification.

The above benzene solution was diluted to 100 ml. with benzene and 20 g. of anhydrous aluminum chloride added. The reaction mixture was heated to reflux temperature for two hours and the suspension poured into a mixture of 12N hydrochloric acid and ice. The volatile constituents were removed from this mixture by evaporation and 2,3,4,5-tetrahydroxybenzonitrile, formed in the above reaction, was extracted into ethyl acetate. The ethyl acetate extract was dried and the residue obtained by removal of the ethyl acetate was recrystallized from water. Three grams of 2,3,4,5-tetrahydroxybenzonitrile were obtained which decomposed at 219° C. yield =36% from the starting 3,4,5-trimethoxysalicylamide.

Analysis Calculated (for one-fourth mole of water):
C, 48.99; H, 3.02; N, 8.16;
Found: C, 49.06; H, 3.23; N, 8.14.

2,3,4,5-tetrahydroxybenzamide was prepared by careful hydrolysis of the corresponding nitrile in concentrated hydrochloric acid at 60° C. The amide gradually precipitated from a solution of 1.5 g. of the nitrile in 25 ml. of hydrochloric acid. After recrystallization from water, the product decomposed at 290° C. Yield=23%.

Analysis Calculated: C, 45.41; H, 3.81; N, 7.56;
Found: C, 44.83; H, 3.88; N, 7.27.

The above procedure can be adapted for the preparation of other tetrahydroxybenzonitriles, although isomer separation procedures may be necessary where two monobromo substitution products are possible in the starting trimethoxybenzoic acid. Thus, 2,3,5,6-tetrahydroxybenzonitrile can be prepared from 2,3,5-trimethoxybenzoic acid (with 2,3,4,5-tetrahydroxybenzonitrile as a contaminant). Likewise, 2,3,4,6-tetrahydroxybenzonitrile can be prepared from 2,3,4-trimethoxybenzoic acid.

PREPARATION IV

Preparation of Pentahydroxybenzonitrile

Eleven and three-tenths grams of pentamethoxybenzamide obtained by the procedure of Dallacher, *Ann.*, 665, 78–83 (1963) were dissolved in 50 ml. of ethyl acetate to which 10 ml. of thionyl chloride had been added. The reaction mixture was heated to reflux for about three hours. Evaporation of volatile constituents in vacuo yielded a residue comprising pentamethoxybenzonitrile melting at 64° C. after recrystallization from methanol/water; yield=80%

Analysis Calculated: C, 56.92; H, 5.97; N, 5.53;
Found: C, 56.92; H, 5.88; N, 5.49.

Four and three-tenths grams of pentamethoxybenzonitrile were refluxed in 12.5 g. of anhydrous aluminum chloride and 125 ml. of toluene for three hours after which time the suspension was poured into a mixture of 50 ml. of 12N aqueous hydrochloric acid and 200 g. of ice. The toluene layer was separated and the product recovered from the aqueous layer by filtration. Recrystallization from an ethyl acetate/toluene solvent mixture yielded pentahydroxybenzonitrile decomposing at 238° C. with a prior slight decomposition at 220° C.; yield=66%

Analysis Calculated (for monohydrate):
C, 41.80; H, 3.51; N, 6.96;
Found: C, 42.20; H, 3.54; N, 6.94.

Following the procedure of Example 3, ethyl tetrahydroxybenzamidate can be prepared from the corresponding nitrile.

Also following the above procedure, pentahydroxybenzamidate can be prepared from the corresponding pentahydroxybenzonitrile by reaction with ethanol in the presence of anhydrous HCl. The compound is converted to the hydrochloride salt and isolated as such according to the procedure of Example 3.

Compounds represented by formula I above have the ability to inhibit ribonucleotide reductase, an enzyme involved in the reductive conversion of ribonucleotides to deoxyribonucleotides. This enzymatic reaction is a rate controlling step in the biosynthetic pathway leading to DNA and cell replication. In general, the ribonucleotide reductase level is closely correlated with cellular replication. Thus, it is not surprising that the compounds of this invention, which are potent ribonucleotide reductase inhibitors, are also capable of prolonging the life of mice carrying transplanted tumors since replication of tumor cells is equally inhibited. In particular, we have found that administration of a compound of this invention coming within the scope of formula I above prolongs the life of mice inoculated with L1210 leukemia, a tumor not ordinarily susceptible to chemotherapy. In addition, the compounds have shown activity against P388 leukemia and B16 melanoma.

The results of biological tests of compounds according to formula I are incorporated in a series of Tables which follow. Table 1 gives ribonucleotide reductase data for representative compounds of formula I. In the table, column 1 gives the substitution pattern in the benzene-ring, column 2, the $(CHR'')_m$ group, column 3, the

group, and column 4, the $ID_{50}$ (inhibitory dose in micromolar concentration which inhibits ribonucleotide reductase by 50%) in $\mu$moles.

TABLE 1

(OH)$_n$-C$_6$H — $(CHR'')_n$ — C(=R')—R

| $(OH)_n$ | $(CHR'')_m$ | $\overset{R'}{\underset{\|}{C}}$—R | $ID_{50}$ $\mu$M |
|---|---|---|---|
| 3,4 | bond | NOH<br>‖<br>C—NH$_2$.HCl | 8 |
| 3,4 | bond | NH<br>‖<br>C—OEt.HCl | 12 |
| 3,4 | bond | NH<br>‖<br>C—NH$_2$.HCl | 20 |
| 3,4 | bond | NOH<br>‖<br>C—NHOH.HCl | 40 |
| 3,4,5 | bond | NOH<br>‖<br>C—NH$_2$.HCl | 5 |
| 3,4,5 | bond | NH<br>‖<br>C—OEt.HCl | 15 |
| 3,4,5 | bond | NH<br>‖<br>C—NH$_2$.HCl | 25 |

TABLE 1-continued (OH)$_n$-C$_6$H — $(CHR'')_n$ — C(=R')—R

| $(OH)_n$ | $(CHR'')_m$ | $\overset{R'}{\underset{\|}{C}}$—R | $ID_{50}$ $\mu$M |
|---|---|---|---|
| 3,4 | bond | NOH<br>‖<br>C—NH$_2$.H$_2$O | 10 |
| 3,4,5 | bond | NOH<br>‖<br>C—NHOH.HCl | 25 |
| 2,3,4 | bond | NOH<br>‖<br>C—NH$_2$.HCl | 7 |
| 2,3 | bond | NOH<br>‖<br>C—NH$_2$.HCl | 18 |

In the above determination of $ID_{50}$'s in Table 1, ribonucleotide reductase is partially purified from HeLa cells or Ehrlich ascites cells by a procedure similar to that set forth by Elford et al. *J. Biol. Chem.*, 245, 5228 (1970). The activity of the enzyme was measured by a slightly modified assay procedure originally developed by Reichard et al. *id*, 236, 1150 (1969). This procedure measures the conversion of CDP to dCDP. The assay mixture (0.34 ml.) contains 3 $\mu$Ci of [$^3$H] CDP (specific activity 14–19 Ci/$\mu$mol), 3.3 $\mu$mole ATP, 5.9 $\mu$moles magnesium chloride, 8.8 $\mu$moles Hepes buffer at pH=7.5, 15 $\mu$moles dithiothreitol and enzyme protein between 0.4 and 1.3 mg. Incubation was provided for forty minutes at 30° C. Ion exchange chromatography employing Dowex 50 (H$^+$) resin is used to separate the product from the substrate. The inhibitors were dissolved in water and a mixture of water and up to 1% ethanol or 2% dimethylsulfoxide, neither one of which inhibited the enzyme at these concentrations. Each inhibitor was tested at a minimum of three concentrations and the active compounds reassayed at least one additional time. $ID_{50}$'s ($\mu$molar) were estimate from graphs summarizing results for each compound.

Testing of the compounds of this invention against L-1210 lymphoid leukemia were carried out as follows: L-1210 leukemia was maintained by weekly passage of $10^5$ L-1210 cells intraperitoneally into DBA/2 mice. Diluted ascitic fluid, 0.1 ml. ($10^5$ cells), was administered ip to female B6D$_2$F$_1$ mice weighing about 20 g. Drugs were administered ip 24 hours after tumor transplantation and injections were continued daily for a total of eight days. A group of control mice receiving only the injection medium were maintained. Table 2 which follows gives the antitumor activity against L-1210 leukemia for certain compounds of this invention. In the table, column 1 gives the name of the compound, column 2 the dose in mg./kg., and column 3 the percent increase in survival time over controls at each dose level.

TABLE 2

ANTITUMOR ACTIVITY IN L1210 LEUKEMIA

| Name of Compound | Dose in mg/kg | % Increase in Survival Time |
|---|---|---|
| 3,4-dihydroxybenzamidoxime-HCl | 157 | 132.0 |
| | 200 | 43.5 |
| | 238 | 46.9 |
| | 300 | 73.9 |
| 3,4,5-dihydroxybenzamidoxime-HCl | 59 | 90.0 |
| | 132 | 54.5 |
| | 196 | toxic |
| | 220 | 63.6 |
| | 275 | 30.6 |
| 2,3,4-trihydroxybenzamidoxime-HCl | 100 | 38.9 |
| | 200 | 36.1 |
| | 218 | 67.7 |
| | 300 | toxic |
| ethyl 3,4-dihydroxybenzamidate-HCl | 218 | toxic |
| | 327 | toxic |
| | 435 | toxic |
| ethyl 3,4,5-trihydroxybenzamidate-HCl | 300 | 42.3 |
| | 450 | 58.4 |
| 3,4-dihydroxybenzamidine-HCl | 52 | 26.8 |
| | 100 | 58.3 |
| | 104 | 34.1 |
| | 200 | 41.7 |
| | 300 | 47.2 |
| | 400 | 47.8 |
| | 603 | 83.0 |
| 3,4,5-trihydroxybenzamidine-HCl | 200 | 43.5 |
| | 300 | 10.2 |
| 3,4-dihydroxybenzohydroxyamidoxime-HCl | 155 | 39.0 |
| | 200 | 47.8 |
| | 300 | 41.3 |
| 3,4,5-trihydroxybenzohydroxyamidoxime-HCl | 100 | 47.2 |
| | 200 | 55.6 |
| | 300 | 63.9 |
| 3,4-dihydroxybenzohydroxymandel amidoxime-H₂O | 435 | 45.2 |
| | 606 | 45.2 |
| 2,3-dihydroxybenzamidoxime-HCl | 300 | toxic |

3,4-Dihydroxybenzamidoxime and 3,4,5-trihydroxybenzamidoxime were subjected to a further series of tests against various transplanted tumors in mice according to the following protocols:

For L-1210 lymphoid leukemia, 20 grams CDF$_1$ or BDF$_1$ mice rejected ip with 10$^5$ leukemia cells. The drug was given one day after tumor inoculation continued for an additional eight days. The mean survival time for the treated animal was compared to that of the control group. Table 3 which follows gives the results of this test for the above two compounds. In the table, column 1 gives the name of the compound, column 2 the dose levels, and column 3 treated over control percent survival time. (In other words, a figure of 175 indicates a 75% increase in survival time.)

TABLE 3

Activity vs L-1210 Leukemia

| Name of Compound | Dose mg/kg | t/c % |
|---|---|---|
| 3,4-dihydroxybenzamidoxime.HCl | 400 | toxic, 200*202 |
| | 300 | 113 |
| | 200 | 175, 128, 155, 186 |
| | 100 | 128, 132, 141, 133 |
| | 50 | 137, 117, 132, 146 |
| | 25 | 130 |
| 3,4,5-trihydroxybenzamidoxime.HCl | 200 | 212, 182 |
| | 100 | 152, 137 |
| | 50 | 138, 137 |
| | 25 | 136, 121 |

*t/c % greater than 130 are significant

The drugs were also used to treat melanotic melanoma B$_{16}$. The protocol for testing against this tumor is as follows:

0.5 ml. of a tumor homogenate prepared by homogenizing 1 g. of tumor with 10 ml. of cold balanced solution is implanted ip in groups of 10 B$_6$C$_3$F$_1$ mice. The drug is administered daily for a total of nine days starting one day after tumor inoculation. The results are expressed as mean survival time of treated group versus control group (T/C) as a percent. Table 4 which follows gives the results of this test.

TABLE 4

Activity vs B$_{16}$ Melanoma

| Name of Compound | Dose mg/kg | T/C % |
|---|---|---|
| 3,4-dihydroxybenzamidoxime.HCl | 400 | 117 |
| | 200 | 134 |
| | 100 | 129 |
| | 50 | 127 |
| | 25 | 119 |
| | 800 | toxic |
| ethyl gallamidate.HCl | 400 | 124, 156, 137 |
| | 200 | 121, 125, 122 |
| | 100 | 121, 109, 107 |
| | 50 | 109, 104 |
| | 25 | 105 |

*T/C % greater than 120 are significant.

A compound of this invention was also tested on the solid colon tumor model, colon 38. The tumor was implanted subcutaneously and the drug injected intraperitoneally twice a day on day two (seven hours apart) and twice on day nine. The median tumor weight estimated from tumor diameter is the parameter of tumor inhibition and is measured on day 20. The median tumor weight of treated versus control=T/C percent. Table 5 which follows gives the results of this test.

TABLE 5

Activity vs Colon 38

| Name of Compound | Dose mg/kg | T/C % |
|---|---|---|
| 3,4-dihydroxybenzamidoxime.HCl | 800 | 87 |

Lower doses were ineffective.

Compounds of this invention also showed some activity against P388 leukemia. The following protocol was used:

CDF$_1$ mice were injected ip with 10$^6$ cells The drug was administered in the first day after tumor inoculation and continued daily for five treatments. The mean survival time of the treated group compared to the non-treated control group equals T/C×100=T/C percent. Table 6 which follows gives the results of these determinations.

TABLE 6

Activity vs P388 Leukemia

| Name of Compound | Dose mg/kg | T/C %* |
|---|---|---|
| 3,4,5-trihydroxybenzamidoxime.HCl | 400 | toxic |
| | 300 | 163 |
| | 200 | 155, 155, 177 |
| | 100 | 150, 154, 138, 148 |
| | 50 | 142, 138, 141 |
| ethyl gallamidate.HCl | 400 | 149, 160 |
| | 200 | 139, 123 |
| | 100 | 129, 128 |
| | 50 | 114 |
| | 25 | 112 |

TABLE 6-continued

| Activity vs P388 Leukemia | | |
|---|---|---|
| Name of Compound | Dose mg/kg | T/C %* |
| | 12.5 | 104 |

*T/C % over 130 are considered significant

It is believed that the antineoplastic activity of the compounds of this invention is due in parts to their ability to scavenge free-radicals. Additionally, the compounds of this invention are cancer protective agents and this utility also may be a manifestation of their free-radical scavenging capability. Free-radical scavenging agents may also be useful in detoxifying mammals in whom an excess of free radicals is a cause and/or result of the toxicity. Other possible uses of free radical scavengers are to inhibit protaglandin transformation, leucotriene interconversion and lipogenesis, to act as inflammatory modulators and as food additive or preservatives to prevent lipid oxidation. The free radical scavenging ability of the compounds of the invention was determined by measuring the destruction of the stable free radical, diphenylpicrylhydrazyl, in the presence of the test compound in a manner similar to that reported by Venker and Herzmann, *Naturwiss*, 47, 133–134 (1960). The absorbance at 518 nM of a 100 μM solution of diphenylpicrylhydrazyl free radical in acetone was monitored in a Gilford spectrophotometer. The test compound was added at a final concentration of 25 μM and the rate of reduction of absorpotion at 518 nM was observed. Table 7 below gives the free radical scavenging abilities of the compounds of this invention expresses as the initial rate of decrease in optical density units/min.

TABLE 7

FREE RADICAL SCAVENGING ABILITIES

| Compound | Initial Δ units/min.* (518 nm) |
|---|---|
| 3,4-dihydroxymandelamidoxime | 0.383 |
| 3,4-dihydroxybenzamidoxime.HCl | 0.718 |
| 3,4,5-trihydroxybenzamidoxime.HCl | 0.929 |
| Ethyl 3,4,5-trihydroxybenzamidate.HCl | 3.730 |
| Ethyl 3,4-dihydroxybenzamidate.HCl | 0.706 |
| 3,4-dihydroxybenzamidine.HCl | 1.721 |
| 3,4,5-trihydroxybenzohydroxyamidoxime.HCl | 0.882 |
| 3,4,5-trihydroxybenzamidine.HCl | 4.912 |

*One optical density unit decrease of initial absorbance/min at 518 nm by 2.5 μM of agent.

Additional free radical scavenging potential of a compound of this invention was measured on a generated tyrosine free radical. There is evidence that a tyrosine free radical is formed as part of the mammalian ribonucleotide reductase enzyme during the conversion of ribonucleotides to deoxyribonucleotides—see L. Äkerblom, et al. *Proc. Natl. Acad. Sci. USA*, 78, 2159–2163 (1981). The method for the generation of the tyrosine free radical and its destruction by a compound of this invention was accomplished by pulse radiolysis experiments at Brunel University, Oxbridge England on the Brunel 4 MeV linear accelerator using a 1.5 cm optical cell and a 200 ns pulse delivering a dose of approximately 1 krad as measured by thiocyanate dosimetry. All solutions were purged with nitrogen using a syringe-deaerating technique prior to use. The detailed description of the methodology can be found in R. L. Willson, *Chemistry and Industry*, 183–193 (1977).

For the generation of the tyrosine radical, sodium azide was utilized as an intermediate between the pulse radiolysis generated free electron and tyrosine. Hydroxyurea was used as a reference point for the ability of these compounds to scavange tyrosine free radical since hydroxyurea inhibition of ribonucleotide reductase has been attributed to its ability to scavenge the free radical of the active mammalian ribonucleotide reductase.—see Äkerblom et al (loc. cit). See also I. K. Larsen et al., *Eur. J. Biochem*, 125, 75–81 (1982). A rate constant of $1.9 \times 10^6 \, m^{-1} S^{-1}$ was determined for hydroxyurea and $4.5 \times 10^8 \, M^{-1} \, S^{-1}$ for 3,4-dihydroxybenzamidoxime hydrochloride. In other words, 3,4-dihydroxybenzamidoxime hydrochloride was 100+ times a faster scavenger of tyrosine free radical than hydroxyurea. The compounds, according to Formula I, have the ability to destroy the superoxide ($O_2^-$) radical generated in vitro, as set forth below:

The rate of production of superoxide from the xanthine oxidase reaction or from human leukocytes activated with phorbol myristate acetate was measured spectrophotometrically as the superoxide dismutase (SOD)-inhibitable portion of the reduction of ferricytochrome c or nitroblue tetrazolium (NBT). All assays were carried out at 37° C., pH 7.1. For the superoxide production by the xanthine oxidase reaction, a concentration of 0.04 U/ml of xanthine oxidase was used with 0.1 mM xanthine as substrate. Absorbances were measured in the presence of 30 U/ml of SOD and in its absence. The indicators were either ferricytochrome c or NBT in a concentration of 20 uM. The initial rate of reduction of NBT was monitored at 530 nm and that of cytochrome c at 550 nm. Extinction coefficients were $21.4 \times 10^3/M$ cm for cytochrome c and $17.9 \times 10^3/M$ cm for NBT. The initial rate of production of superoxide from leukocytes was measured using a concentration of 20 uM ferricytochrome c or NBT as described above in the presence and absence of 30 U/ml of SOD.

EFFECT OF 3,4,5-TRIHYDROXYBENZAMIDATE ON SUPEROXIDE GENERATION IN VITRO

| | Measuring System | |
|---|---|---|
| Treatment | Cytochrome C Reduction (nmoles) | NBT Reduction (nmoles) |
| Control | 7.55 | 8.50 |
| 10 uM | 4.89 | 7.60 |
| 20 uM | 3.21 | 6.10 |
| 50 uM | 2.22 | 3.67 |
| 100 uM | 1.91 | 1.78 |
| 200 uM | | 1.45 |
| 500 uM | | 1.23 |
| SOD | 0.70 | 2.01 |

EFFECT OF 3,4,5-TRIHYDROXYBENZAMIDOXIME ON SUPEROXIDE GENERATION IN VITRO

| | Measuring System | |
|---|---|---|
| Treatment | Cytochrome C Reduction (nmoles) | NBT Reduction (nmoles) |
| Control | 6.00 | 6.44 |
| 10 uM | 4.73 | 5.35 |
| 20 uM | 4.56 | 5.06 |
| 50 uM | 5.38 | 2.55 |

-continued

| Treatment | Measuring System | |
|---|---|---|
| | Cytochrome C Reduction (nmoles) | NBT Reduction (nmoles) |
| 100 uM | 6.06 | 1.14 |
| 200 uM | 6.50 | 0.81 |
| 300 uM | 6.25 | 0.71 |
| 500 uM | 5.81 | 0.87 |
| SOD | 0.44 | 1.23 |

The novel nitriles and amide starting materials for the synthesis of the compounds of this invention, (Formula I wherein n is 4 or 5), although chiefly useful as intermediates, have ribonucleotide reductase inhibitory activity which results in antitumor activity and are also active free radical scavengers.

Table 8 which follows gives anti-tumor data vs L-1210 and P-388 leukemia for these novel nitriles.

TABLE 8

| | Antileukemia Activity | |
|---|---|---|
| Name of Compound | Dose in mg/kg | % Increase in Survival Time |
| | L1210 | |
| 3,4-dihydroxybenzonitrile | 47.6 | 4.7 |
| | 95.2 | 15.6 |
| | 196 | Toxic |
| 2,3,4-trihydroxy-benzonitrile | 50 | 11.0 |
| | 100 | 26.0 |
| | 155 | 12.1 |
| | 259 | Toxic |
| | 327 | Toxic |
| 3,4,5-trihydroxy-benzonitrile | 118 | 34.0 |
| | 157 | 28.0 |
| 2,3,4,5-tetrahydroxy-benzonitrile | 163 | 48.4 |
| | 230 | Toxic |
| pentahydroxybenzonitrile | 34.3 | 14.2 |
| | 51.5 | 0 |
| | 77.2 | Toxic |
| | 116.0 | Toxic |
| | P-388 | |
| 3,4,5-trihydroxy-benzonitrile | 400 | 26 |
| | 200 | 26, 39 |
| | 100 | 10, 39 |
| | 50 | 15, 20 |

Use of Free-Radical Scavengers of This Invention in Treating Ischemia

Ischemia is defined as a deficiency of blood in a body part or tissue caused by a functional constriction or actual blockage of a blood vessel. One of the chief functions of blood is to carry oxygen to body parts. Ischemia therefore decreases oxygen supply in the affected body part. This lack of oxygen rapidly results in tissue damage shortly followed by tissue necrosis. In the brain, ischemia can be caused by congenital anomalies, atherosclerosis, intracranial thrombosis, etc. If the ischemia lasts for more than a few minutes, infarction results with consequent permanent neurologic damage.

Ischemia also plays a major role in heart disease. For example, Angina pectoris is caused by myocardial ischemia. Ischemia associated with thrombus-induced coronary artery disease produces infarction followed rapidly by ischemic myocardial necrosis. The extent of myocardial post-ischemic damage can be diminished by lessening the oxygen demand of myocardial tissue by means of beta-blockers. Another current therapy of coronary artery disease has involved dissolution of the obstructive thrombus. For this purpose, enzymes such as streptokinase and urokinase have been used as well as treatment with TAP (tissue-type plasminogen activator). It has been found, however, that simple restoration of blood flow or decreasing the tissue oxygen demand does not prevent post-ischemic myocardial injury because there are additional mechanisms the body uses to increase tissue oxygen supply. This mechanism is called reperfusion and the process cumulatively damages tissue. The whole process is called ischemic reperfusion injury. (The same situation is found with ischemia in the brain.) During this process, the body produces oxygen free radicals ($O_2^-$), peroxides, etc. The production of these oxygen-rich products are discussed in articles by Hammond and Hess, J. A. C. C. 6 215 (1985) and Halliwell, FASEB J. 1 358 (1987). Halliwell disdains the use of antioxidants in preventing reperfusion ischemic injury but suggests either using enzymes such as superoxide dismutase or glutathione peroxidase or inhibitors of the enzyme xanthine oxidase. He also suggests using chelating agents such as 2,3-dihydroxybenzoate. According to Halliwell, Luchesi, et al have suggested using inhibitors of arachidonic acid metabolism, calcium ion chelators and anti-oxidants to prevent reperfusion ischemic injury. All offered some protection against reoxygenation injury in the heart.

Simpson, et al., Fed. Proc. 46 2413 (1987) suggest using free radical scavengers such as N-(2-mercaptopropionyl)glycine to prevent free radical production in myocardial ischemia.

U.S. Pat. No. 4,668,676 claims the use of azapropazone, a known xanthine oxidase inhibitor which can also inhibit $O_2^-$ free radical production by activated polymorphonuclear leukocytes, in preventing ischemic and post-ischemic tissue damage.

The compounds of this invention, as represented by the above formula, are useful in treating ischemia reperfusion injury, presumably because of their free-radical scavenging ability. The following protocol illustrates this activity on the ischemia produced during treatment of coronary artery disease.

Female New Zealand white rabbits (2 kg) were heparinized and anesthetized and their hearts removed. The isolated rabbit hearts were perfused by the method of Langendorff at a constant pressure of 80 mm Hg with a Krebs-bicarbonate-buffered perfusate which was bubbled with 95% $O_2$, 5% $CO_2$ gas. Chelex-treated perfusate was prepared by eluting the solution through a column of chelex 100 resin which was pre-equilibrated with 4 volumes of the perfusate solution. All perfusate solutions were routinely filtered through 0.8 um millipore filters prior to use. Heart rate and left ventricular developed pressure were measured using a fluid-filled balloon secured into the left ventrile. The balloon was connected to a Statham P23 DB pressure transducer via a hydraulic line and the transducer output amplified to a strip chart recorder. The ventricular volume was adjusted to achieve a left ventricular end disastolic pressure of 12 mmHg. During periods of global ischemia, the balloon was deflated and then reinflated 15 min after reflow.

The spin trapping studies were performed by infusing the spin trap 5,5-dimethyl-1-pyrroline-N-oxide (DMPO) perfusate solution through a side arm located just proximal to the end of the heart perfusion cannula.

EPR spectra were recorded in flat cells at room temperature with either Varian E-9 or Bruker-IBM ER 300 spectrometers operating at X-band using 100 kHz modulation frequency and with TE 104 or TM 110 cavities.

The microwave frequency and magnetic field were precisely measured using a Hewlett Packard 5342A Microwave Frequency counter and Bruker ER 035M NMR Gaussmeter. Spectral simulations were performed using simulation programs which assume isotropic g and A tensors, written in either basic or asyst. Quantitation of the free radical signals was performed by comparing the double integral of the observed signal to that of a known concentration of the tempo free radical in aqueous solution. These measurements were performed with the same flat cell using nonsaturating microwave power.

RESULTS

After removal of the heart from the donor animals and cannulation, a 15-min period of control perfusion was allowed for the hearts to reach stable left ventricular function with developed pressures of 110+10 mm Hg. Subsequently perfusate containing 40 mM DMPO was administered for a period of 1 min, and the effluent perfusate sampled in a 10-S aliquots. No EPR signal was observable in either the DMPO-containing perfusate solution or in any of the 10 s samples of effluent perfusate. After an additional 10 min, the hearts were subjected to 30 min of global ischemia followed by reperfusion in the presence of 40 mM DMPO. At the onset of reperfusion perfusate was again sampled in 10-s aliquots and EPR measurements performed. After 10-20 s of reperfusion, a prominent EPR spectrum was observed. In determining the efficacy of 3,4,5-trihydroxybenzamidoxime (VF233), the test system consisted of 16 Langendorff perfused rabbit hearts subjected to 30 min of normothermic (37°) global ischemia followed by 45 min reperfusion. Just prior to reperfusion one-half of the hearts received a bolus of 10 mM solution of 3,4,5-trihydroxybenzamidoxime dissolved in saline, followed by 100 uM of 3,4,5-trihydroxyamidoxime over the first min of reperfusion. The control hearts received a bolus of saline just prior to reflow. Treated hearts recovered 67±9 mm Hg of pre-ischemic control developed pressure as compared to 49±9 mm Hg in control hearts (p<0.01) (Table 9). Simultaneously, EPR studies were performed using the spin trap DMPO. Hearts were infused with 40 mM DMPO and EPR spectra performed on the coronary effluent. Prior to ischemia during control perfusion, no signal was observed. However, upon reperfusion a prominent EPR spectrum was observed peaking at 10-20 sec of reflow and then decreasing until after 5 min no signal was seen. This reperfusion signal observed within seconds upon post-ischemic reperfusion consisted of two components: a 1:2:2:1 quartet signal, $a_N = a_H = 14.9$ G, suggestive of DMPO-OH the trapped hydroxyl radical adduct, and a 1:1:1:1:1:1 sextet signal, $a_N = 15.8$ G, $a_H = 22.8$ G, corresponding to DMPO-R the trapped alkyl radical adduct in the coronary effluent of reperfused control hearts. These signals were not observed in hearts reperfused with 3,4,5-trihydroxy-benzamidoxime, suggesting scavenging of ˙OH and ˙R radicals by the drug. There is, however, the appearance of a new radical signal which appears as a single broad peak centered at 3480 G, presumably secondary to the formation of a drug radical. This signal is also observed on reperfusion with the compound alone in the presence of no DMPO. However, it is not observed upon reperfusion in the absence of the drug. In the presence of low modulation amplitude, it is possible to resolve the fine structure of this radical.

TABLE 9

EFFECT OF 3,4,5-TRIHYDROXYBENZAMIDOXIME ON CONTRACTILE FUNCTION IN RABBIT HEART AFTER 30 MIN OF GLOBAL ISCHEMIA AND 45 MIN OF REPERFUSION

| Reperfusion Conditions | Developed Pressure* |
|---|---|
| Perfusate | 49 ± 9 |
| Perfusate + 3,4,5-trihydroxybenzamidoxime | 67 ± 9 |

*Left ventricular developed pressure (mm Hg); 8 animals per group

The compounds of this invention because of their ability to scavenge free-radicals in vivo are capable of modulating inflammation as set forth in the following protocol:

Mice received the test compound topically to each side of the right ear one hr prior to the inflammatory challenge, at which time they were challenged (except for the negative control) with 10 microliter of a 2 mg/20 microliter solution of arachidonic acid applied to each side of the right ear. One hour post-challenge, the animals were sacrificed, the right ears removed, and an 8 mm disc punched from each. These discs were then weighed. The following table gives the results of this experiment.

TABLE 10

ARACHIDONIC ACID INDUCED EAR EDEMA ASSAY

Experiment 1

| Compound Administered | Total Dose mg | Route | Total No. of Mice | Mean Increase in Weight of Inflammed Ear[a] mg ± S.E. | Percent Inhibition[b] |
|---|---|---|---|---|---|
| Positive Control | — | Topical | 10 | 17.0 ± 0.6 | — |
| 3,4,5-trihydroxybenzamidoxime-HCl | 2 | " | 8 | 9.5 ± 0.3[c] | 44 |
| 3,4,5-trihydroxybenzamidine.HCl | 2 | " | 8 | 13.0 ± 0.3[c] | 24 |

[a]Mean ear weight of vehicle (90% acetone, 10% H₂O) treated normal control animals is 8.2 ± 0.2.
[b]vs. positive control
[c]p = .000

Experiment 2

| Compound Administered | Total Dose mg | Route | Total No. of Mice | Mean Increase in Weight of Inflammed Ear[a] mg ± S.E. | Percent Inhibition[b] |
|---|---|---|---|---|---|
| Positive Control | — | Topical | 10 | 19.0 ± 0.5 | — |

TABLE 10-continued
ARACHIDONIC ACID INDUCED EAR EDEMA ASSAY

| | | | | |
|---|---|---|---|---|
| Ethyl 3,4,5-trihydroxybenzamidate.HCl | 2 | " | 8 | 12.3 ± 0.4[c] | 35 |

[a]Mean ear weight of vehicle treated normal control animals is 7.6 ± 0.2.
[b]vs. positive control
[c]p = .000

It is apparent from the preceding results that selected compounds of this invention can moderate the inflammation caused by topical application of arachidonic acid.

In another aspect of their anti-inflammatory activity in vivo, six compounds coming within the scope of this invention were tested for their ability to inhibit delta five lipoxygenase. This enzyme is believed to initiate the synthesis of slow reacting substance of anaphylaxix (SRS-A), an important mediator in the pathogenesis of asthma. Thus, a drug capable of inhibiting this enzyme would also help to prevent asthmatic attacks. In this determination, $\Delta^5$-lipoxygenase was derived from the supernatant fraction of lysed rat basophilic leukemia (RBL-1) cells. The activity of the enzyme was determined by measuring the catalytic conversions of [1-C]arachidonic acid to [1-14C]-5-hydroperoxy-6,8,11,14-eicosatetraenoic acid (([1-14C]-5-HPETE) which leads to the formation of the corresponding 5-hydroxy derivative ([1-14C]-5-HETE). The $\Delta^5$-lipoxygenase was derived from RBL-1 cells which were lysed by homogenization in ice-cold buffer (50 mM Tris-HCl buffer, pH 7.2, containing 1 mM EDTA and 14 uM indomethacin). The homogenate was centrifuged at 4° C. at 49,000 g for 20 min and the resulting supernatant fraction was used as the source of $\Delta^5$-lipoxygenase. The enzyme was assayed at 37° using 6.7 uM (0.39 uCi/ml) [1-14C]arachidonic acid as the substrate in 50 mM Tris-HCl buffer, pH 7.2, containing 1 mM gluthatione, 3 mM CaCl$_2$, 14 uM indomethacin, and 0.25 to 0.50 mM EDTA. The mixture was incubated for 10 min, and the reaction was stopped by the addition of citric acid and diethyl ether. The ethereal extract containing [1-14C]-5-HETE and unreacted substrate was analyzed by silica gel TLC. The effect of compounds on $\Delta^5$-lipoxygenase activity was determined by preincubating the enzyme for 10 min at 30° in the presence or absence of various concentrations of the drug prior to addition of substrate.

THE ABILITY OF COMPOUND TO INHIBIT $\Delta^5$-LIPOXYGENASE

| Compound | Concentration (uM) | Inhibition (%) |
|---|---|---|
| 3,4,5-trihydroxy-benzamidoxime.HCl | 10 | 90 |
| 3,4,5-trihydroxy-benzamidoxime.HCl | 1 | 24 |
| 3,4-dihydroxy-benzamidoxime.HCl | 10 | 94 |
| 3,4-dihydroxy-benzamidoxime.HCl | 1 | 25 |
| Ethyl 3,4,5-trihydroxy-benzamidate.HCl | 10 | 86 |
| 3,4,5-trihydroxy-benzamidine.HCl | 10 | 75 |

Compounds according to this invention were also able to affect SRS-A biosynthesis, also in vivo. In this determination, male Hartley guinea-pigs (200–300 g) were sensitized with a single intraperitoneal injection of ovalbumin (10 mg) in 1 ml of 0.9% w/v NaCl solution (saline). The animals were used for study on days 28–45, following the ovalbumin injection. Guinea-pigs this sensitized were anaesthetized with an intraperitoneal injection of urethane (2 g/kg), and the carotid artery and jugular vein cannulated for measurement of arterial blood pressure and to facilitate intravenous drug administration. Animals were ventilated with a Harvard small animal respirator set at a stroke volume of 2.5 cc and a rate of 40 breaths per min. Ventilatory pressure (cmH$_2$O) was measured with a Statham pressure transducer from a side arm off the tracheal cannula.

Following surgical preparation, the animals were pretreated with indomethacin (10 mg/kg, i.v.) 22 min before ovalbumin challenge presumably to shunt arachidonic acid from the cyclooxygenase pathway into the lipoxygenase pathway for the formation of leukotrienes, and eliminating the modulating effects of protaglandins. Spontaneous breathing was arrested with succinylcholine (1.2 mg/kg) 7 mins before antigen challenge. Treatment with succinycholine resulted in a constant baseline ventilatory pressure of 5–8 cmH$_2$O. The bronchoconstrictor effects of histamine were abolished with pyrilamine (2.0 mg/kg), administered 6 min before antigen challenge. Propranolol was administered 5 min before antigen challenge.

Plasma SRS-A was determined as follows: Arterial blood was drawn from the carotid artery of the guinea-pigs into sodium citrate (0.38%) containing indomethacin ($10^{-4}$ M). Blood volume was replaced with isotonic saline. The blood samples were centrifuged at 1200 g for 15 min at 4° C. The plasma supernatant was decanted and extracted with 4 volumes of absolute ethanol. The precipitated protein was removed by centrifugation at 40,000 g for 30 min at 4° C. The ethanol supernatant was decanted and evaporated to dryness under nitrogen. Samples were redissolved in distilled water for bioassay.

SRS-A was bioassayed on the guinea-pig ileum incubated in Tyrode solution containing $10^{-6}$ M atropine sulphate and $10^{-6}$ M pyrilamine maleate and aerated with 95% O$_2$ and 5% CO$_2$. Changes in tension were measured isotonically with an Adaps rotary motion transducer and recorded on a Linear recorder. The tissue was standardized with chemically synthesized LTE$_4$. The results are given in the following Table.

EFFECT OF DRUG ON SRS-A BIOSYNTHESIS

| Compound | % Inhibition of SRS-A Biosynthesis (10 mg/kg, i.v.) |
|---|---|
| 3,4-dihydroxy-benzamidoxime.HCl | 25 |
| Ethyl-3,4,5-trihydroxy-benzamidate.HCl | 29 |

FORMULATION AND ADMINISTRATION

Treatment of arterial or cerebral ischemia clearly involves administration of the drug at an appropriate concentration in vehicles which are compatible with body fluids including blood; i.e., isotonic solutions. The drugs are not administered continuously but in bursts since the production of damaging free-radicals following arterial blockage or a cerebral accident is not a continuous process. The drugs are administered in a concentration in the range 100 ug to 15 g per liter at the rate of 0.5 to 150 ml per minute for short periods of time. The drugs can be administered by an intraarterial, intravenous, intrathecal or in a perfusate directly into the area of ischemia. For topical application to modulate inflammation, the drugs are preferably dissolved or suspended in a lotion or cream and the material applied directly to the skin. The prevention and treatment of asthmatic attacks can be done by parenteral administration or by inhalation.

The compounds of this invention are administered parenterally to mammals suffering from a neoplastic disease, preferably using a water soluble salt of the drug. Intravenous injection of an isotonic salt solution of the drug salt is the preferred route of administration.

We claim:

1. A pharmaceutical formulation in unit dosage form for parenteral administration containing a compound of the following formula plus one or more pharmaceutically-acceptable excipients

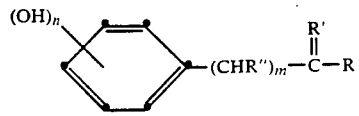

in which n is 2–5m, m is 0 or 1, R" is H or OH, R' is NH or NOH and R is $NH_2$, NHOH or $O$-$C_{1-3}$ alkyl, subject to the provisos that when R' is NH, R can only be $NH_2$ or NHOH and that when R' is NOH, R can only be $NH_2$ or $O$-$C_{1-3}$ alkyl.

2. The method of scavenging free-radicals generated in-vivo in a mammal having a disease condition involving excess free-radical formation which comprises administering to said diseased mammal in a pharmaceutically-acceptable formulation an amount of a compound of the following formula in an amount effective to decrease free-radical concentration

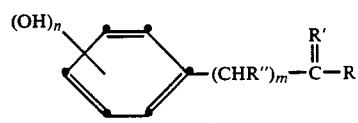

in which n is 2–5, m is 0 or 1, R" is H or OH, R' is NH or NOH, R is $NH_2$, $O$-$C_{1-3}$alkyl or NHOH; subject to the provisos that when R' is NOH, R can only be $NH_2$ or NOH and that when R' is NH, R can only be $NH_2$ or $O$-$C_{1-3}$alkyl, or a salt thereof.

* * * * *